(12) United States Patent
Chen (10) Patent No.: US 7,444,071 B2
(45) Date of Patent: Oct. 28, 2008

(54) METHOD FOR DIAGNOSING DISEASE FROM TONGUE IMAGE

(75) Inventor: Shoupu Chen, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 224 days.

(21) Appl. No.: 11/116,723

(22) Filed: Apr. 28, 2005

(65) Prior Publication Data

US 2006/0247502 A1    Nov. 2, 2006

(51) Int. Cl.
  G03B 41/00    (2006.01)
  G03B 43/00    (2006.01)
  A61B 5/00    (2006.01)
(52) U.S. Cl. .................... 396/14; 348/77; 348/188; 600/300; 600/407; 128/922; 382/128
(58) Field of Classification Search ............. 396/14, 396/16; 600/300, 407; 128/922; 348/77, 348/187, 188
See application file for complete search history.

(56) References Cited

U.S. PATENT DOCUMENTS 5,235,510 A * 8/1993 Yamada et al. ............. 600/300
2004/0151379 A1 * 8/2004 Kim et al. .................. 382/209

FOREIGN PATENT DOCUMENTS

EP    1 450 287    8/2004

OTHER PUBLICATIONS

Giovanni Maciocia; "Tongue Diagnosis in Chinese Medicine" Eastland Press, Seattle, 1996.
C.S. McCamy et al.; "A Color-Rendition Chart" Journal of Applied Photographic Engineering; Vol. 2, No. 3, Summer 1976; pp. 95-99.
Yang Cai; "A Novel Imaging System for Tongue Inspection" IEEE Instrumentation and Measurement, May 2002.
www.gotomypc.com.
Bo Pang et al.; "On Automated Tongue Image Segmentation in Chinese Medicine" 2002 IEEE, pp. 616-619.
Christopher Burges; "A Tutorial on Support Vector Machines for Pattern Recognition" Data Mining and Knowledge Discovery, 2, 1998, pp. 121-167.
Bo Pang et al.; "Computerized Tongue Diagnosis Based on Bayesian Networks" IEEE Transactions on Biomedical Engineering, vol. 51, No. 10, Oct. 2004, pp. 1803-1810.

* cited by examiner

Primary Examiner—W. B. Perkey (57) ABSTRACT

A digital image processing method for a centralized multi-mode medical tongue image inspection system, comprising the steps of: forming at least one service unit (300) for performing tongue record (220) construction; forming a processing unit (320) for tongue record inspection (308); and providing communication links (330) between the service units and the processing unit.

8 Claims, 8 Drawing Sheets
(2 of 8 Drawing Sheet(s) Filed in Color)

METHOD FOR DIAGNOSING DISEASE FROM TONGUE IMAGE

FIELD OF THE INVENTION

The present invention relates generally to a medical imaging system and, in particular, to a longitudinal tongue image inspection system.

BACKGROUND OF THE INVENTION

One of the principal concepts of Chinese medicine is that there are correspondences among various parts of the body. In pulse diagnosis the pulse on the radial artery can be felt in three sections reflecting the energetic states of the upper, middle and lower parts of the body. In facial diagnosis the face is believed to reflect the condition of different organs. In tongue diagnosis the same general principal is applied. Certain parts of the tongue reflect the health of the other parts of the body, or certain internal organs. The beauty of tongue diagnosis lies in its simplicity and immediacy: whenever there is a complex disorder full of contradictions, examination of the tongue instantly clarifies the main pathological process (see "Tongue Diagnosis in Chinese Medicine," by Giovanni Maciocia, Eastland Press, Seattle, 1996).

Tongue diagnosis is a vital instrument used in traditional Chinese medicine (TCM) both for assessing the current health of a patient and providing a basis for prognosis. It also informs the practitioner about the underlying strength or weakness of the patient's constitution.

For thousands of years, tongue diagnosis has played an indispensable role in the practice of traditional Chinese medicine. TCM practitioners rely on tongue diagnosis to differentiate one syndrome from another, and use variations in the tongue's color, texture, shape, and coating to evaluate a patient's condition.

In the practice of TCM, tongue diagnosis is accomplished by visual inspections. Visual inspection of the tongue offers many advantages: it is a non-invasive diagnosis method, is simple, and inexpensive. However, the current practice in TCM is mainly experience based or subjective. The quality of the visual inspection varies between individual practitioners. And although there are a few experts successfully diagnosing cancers based on inspection of the tongue, their skills are not easily transferable to other medical professionals. Their expertise is limited at qualitative descriptions, not to quantitative or mathematical formulations.

Furthermore, traditional visual inspection of the tongue does not provide traceable fidelity information on patients' tongue appearance such as color, coating and texture, except subjective descriptions in writing.

Therefore, there is a need for creating a tongue diagnosis system that facilitates performing functionalities such as tongue image acquisition, recording, retrieval, analysis, detection, tele-inspection, remote access, and so on.

These and other aspects, objects, features and advantages of the present invention will be more clearly understood and appreciated from a review of the following detailed description of the preferred embodiments and appended claims, and by reference to the accompanying drawings.

SUMMARY OF THE INVENTION

Briefly, according to one aspect of the present invention a method for diagnosing diseases by inspecting images of an individual's tongue comprises forming a first image of the tongue and a portion of the individual's face. A second image of the tongue and the portion of the individual's face is formed. A color comparison of the portion of the individuals' face and the second image of the individual's face in the first image is performed. The colors in the second image are matched to the colors in the first image based on the color comparison. At least one disease is diagnosed based on changes in the first tongue image and the second tongue image.

In another embodiment, a digital image processing method for a centralized multi-mode medical tongue image inspection system comprises forming at least one service unit for performing tongue record construction; forming a processing unit for tongue record inspection; and providing communication links between the service units and the processing unit.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

During a typical examination of a patient in TCM, the patient is asked to let the physician inspect the patient's tongue's physical properties. Equipped with an imaging device, the physician takes an image of the patient's tongue. The captured image data and some contextual information available prior to or after the image collection process constitute an image packet 206, shown in FIG. 2. The contextual information will be referred to as metadata. Metadata is analogous to the image header data that accompanies many digital image files.

Figure 2:
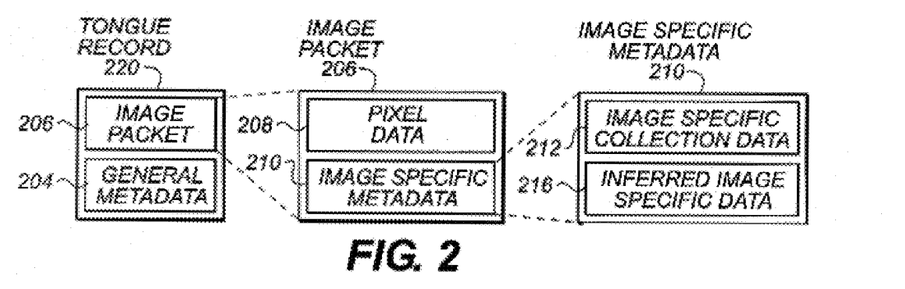
FIG. 2 is an illustration of the concept of a tongue record of the present invention.

The image packet 206 comprises two sections: the pixel data 208 of an image that has been captured by the imaging device, and image specific metadata 210. The image specific metadata 210 can be further refined into image specific collection data 212, and inferred image specific data 216. Image specific collection data 212 contains information such as the image index number, image capture rate, image capture time, image exposure level, and acquisition mode (with or without Munsell ColorChecker, see below). Inferred image specific data 216 includes location and description of identified abnormalities within the image, and any pathologies that have been diagnosed. This data can be obtained either from a physician or by automated methods.

The general metadata 204 contains such information as the date of the examination, the patient identification, the name or identification of the referring physician, the purpose of the examination, suspected abnormalities and/or detection, and any information pertinent to the image packet 206. It can also include general image information such as image storage format (e.g., TIFF or JPEG), number of lines, and number of pixels per line.

Referring to FIG. 2, the image packet 206 and the general metadata 204 are combined to form a tongue record 220 suitable for diagnosis.

It will be understood and appreciated that the order and specific contents of the general metadata or image specific metadata may vary without changing the functionality of the examination bundle.

Figure 3A:
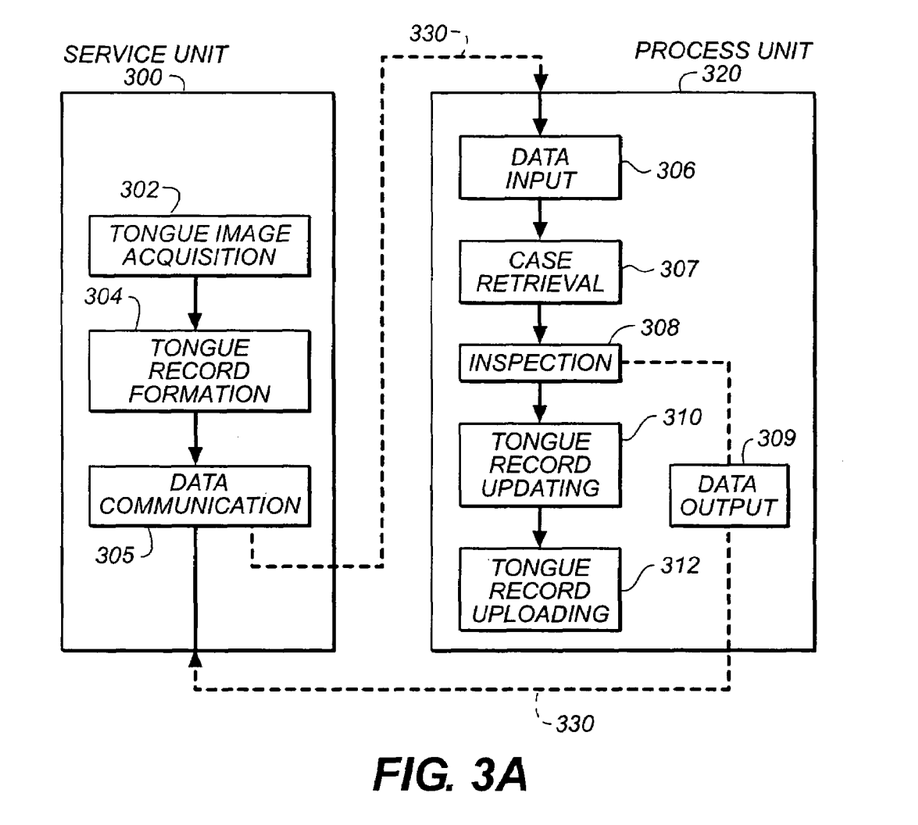
FIG. 3A is a flowchart illustrating information flow of the tongue inspection method of the present invention.
Figure 3B:
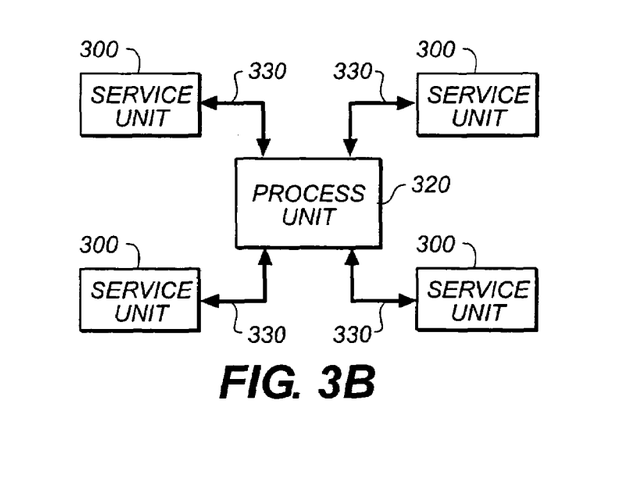
FIG. 3B is an illustration of a centralized tongue image inspection system of the present invention.

Referring now to FIGS. 3A and 3B, an embodiment of the tongue image inspection system of the present invention will be described. FIG. 3A is a flowchart illustrating the tongue image inspection method of the present invention. In FIG. 3B, a service unit 300 consists of an image acquisition step 302, a record formation step 304, and a communication step 305. A tongue image 208 is captured in a tongue image acquisition step 302. In a step of tongue record formation 304, the image 208 is combined with image specific data 210 to form an image packet 206. The image packet 206 is further combined with general metadata 204 and compressed to become a tongue record 220.

The service unit 300 can be of a modular structure including hardware and software physically residing in a TMC practitioner's office, a family doctor's office, a nursing house, a patient's home, a remote site clinic, a medical kiosk, an examination room in a hospital, or in any locations that are able to accommodate such a modular and provide a certain type of data communication link 330 that is to be discussed later.

It is understood by the people skilled in the art that the service unit 300 can be of any forms of combination of an image capturing device and a stand-alone data-editing device. An image capture device can be an off-the-shelf consumer camera, a professional camera, a specially designed camera with data-editing capabilities, or a medical image scanner. A stand-alone data-editing device can be a personal computer, a hand-held computing machine, or a networked computing facility. The image capture device can be physically attached to the stand-alone data-editing through a USB link, an Ethernet cable, a serial communication cable, or a parallel communication cable. The image capture device can also be wirelessly connected to the stand-alone data-editing through. RF communication channel, infra-red, or microwave communication links.

Multiple image acquisition modes are employed in step 302 for the tongue image acquisition method of the present invention. One exemplary mode is to acquire tongue images together with a Munsell ColorChecker (see "A Color Rendition Chart", by C. S. McCamy et al, Journal of Applied Photographic Engineering, Vol. 2, No. 3, pp. 95-99, 1976) embedded in the image. Since the color value of the test cells of the ColorChecker is known, the color of the tongue image can be calibrated computationally (see "A Novel Imaging System for Tongue Inspection", by Yang Cai, IEEE Instrumentation and Measurement Technology Conference, Anchorage, Ak., USA, pp. 21-23, May 2002).

A second exemplary mode of image acquisition is to acquire a tongue image together with a Munsell ColorChecker embedded in the image only once (preferably the first time) for a patient. Subsequent acquisitions of tongue images for the same patient can be made without the use of the Munsell ColorChecker.

A third exemplary mode of image acquisition is to acquire tongue images without the use of the Munsell ColorChecker (calibration could be done by using a statistically satisfied skin color value for a particular population of patients).

Figure 1:
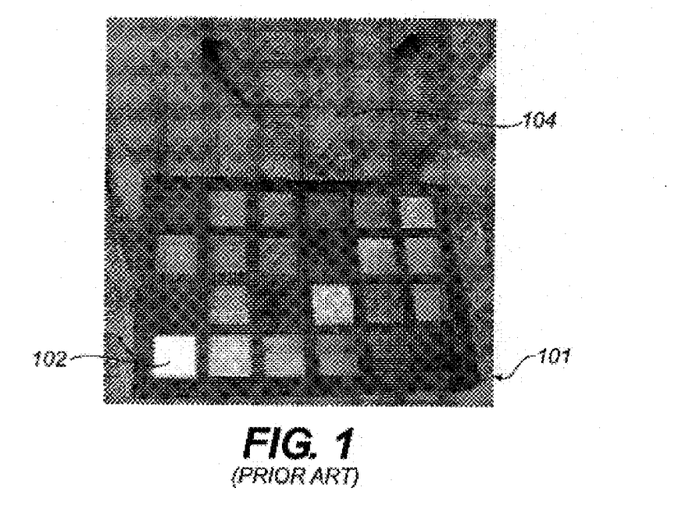
FIG. 1 (Prior Art) is a graph illustration of a tongue image acquisition setup.

For the first and second acquisition mode, an exemplary set up of a prior art (Cai's paper) is shown in FIG. 1. A ColorChecker plate 102 is placed near the patient's tongue 104. The standard color values of all the colors (24 of them) are given for the ColorChecker 102. Cai's method for calibrating the tongue image 104 is by manually clicking the four corners of the ColorChecker 102 in image 101 to get the measured values of those four colors in the captured image 101. By using the given standard color values and the measured color values for the four corners, a transformation function can be derived (see Cai's paper). The derived transformation function is then applied to all the pixels in the image 101 so that the tongue image 102 can be color calibrated for proper visual inspection. The need of color calibration is mainly for color appearance consistency (consistent rendering) of tongue images taken at different times and under various illumination conditions.

As stated previously, in the second acquisition mode, for a patient, the ColorChecker is required when acquiring some images (e.g. a first tongue image). All the subsequent tongue images are taken without a ColorChecker. With the help of the ColorChecker, the first tongue image of this patient can be calibrated in the same manner as the tongue images acquired using the first acquisition mode. Subsequent images can be color calibrated using the first image that is calibrated already with a method called consistent color rendering to be discussed next.

Removing the requirement of acquiring images with a ColorChecker (in the second and third modes) allows the patient to take tongue pictures anytime and anywhere under a normal lighting condition. To still meet the requirement of appearance consistency for tongue images taken in the second and third modes, an operation of consistent rendering is applied to all the tongue images taken without a ColorChecker. In the second acquisition mode, the calibrated first tongue image is then used as a color reference image for subsequently acquired tongue images for the same patient. In the third acquisition mode, any one of the tongue images of a patient can be used a color reference image for the other tongue images for the same patient.

The operation of consistent color rendering for tongue images acquired with the second and third modes can be explained using an exemplary algorithm discussed next with the help of FIG. 5.

Figure 5:
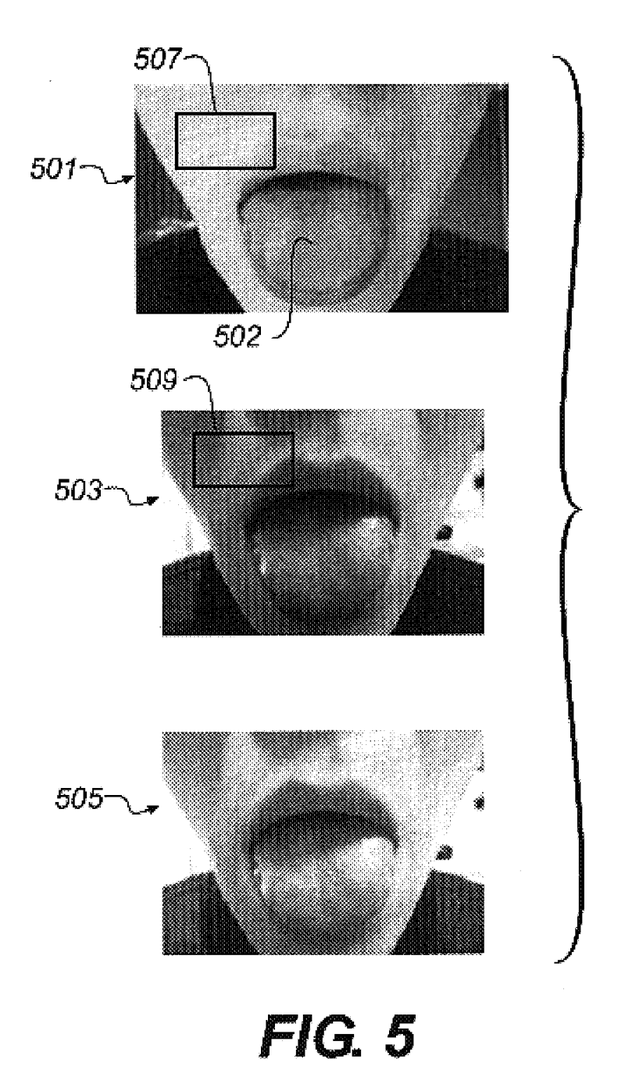
FIG. 5 is an illustration showing tongue image color calibration of the present invention.
Figure 6A:
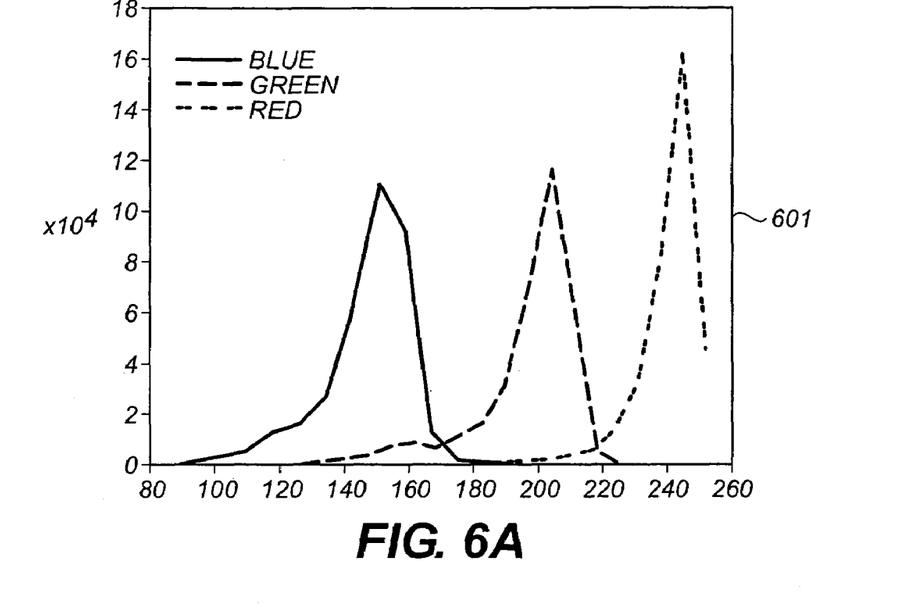
FIGS. 6A and 6B are illustrations of two graphs related to color distributions.
Figure 6B:
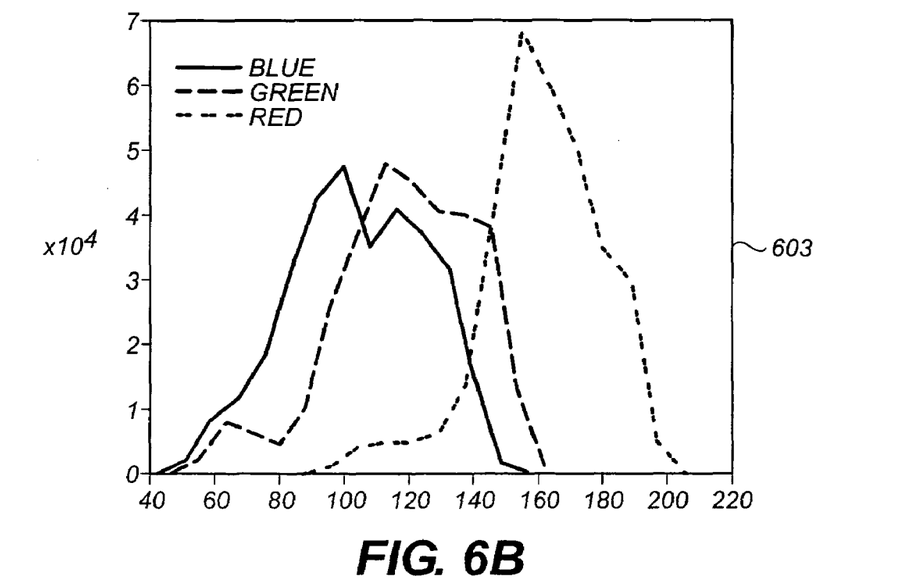

In FIG. 5, there are shown three tongue images of a person. Images 501 and 503 are the original images acquired at different times with different lighting conditions. It is noticeable that the color appearance is quite different for these two images, which may not be acceptable for diagnosing longitudinal changes. Color calibration (consistent color rendering) is thus needed to bring color appearances of these two images to close to each other. The idea is to use color information of a common area (such as patches 507 and 509) from both images to find the color difference. Then use the color difference information to calibrate either one of the images in the color space to make the color appearance closer to the other one. Denote an image by $I_t, t \in [0,1,\ldots T]$. The subscript t signifies the time index for images. The parameter T is the number of images involved in calibration operation. For the current example, T=2. Similarly, denote a patch (such as patches 507 or 509) by $p_t, t \in [0,1,\ldots T]$ for $I_t$. A reference image needs to be selected in order to calibrate other images to have similar color appearance close to the reference image. The reference image is selected arbitrarily or purposely and denoted by $I_r, r \in [0,1,\ldots T]$. Accordingly, the patch associated with the reference image is denoted by $P_r$. Since color images are to be dealt with, to further differentiate color channels (red, green and blue channels), a superscript is introduced to the defined notations. Therefore, a color image is expressed as $I_t^i, t \in [0,1,\ldots T], i \in [1,2,3]$. An exemplary association of a superscript and a color channel could be $I^1$ for a red channel, $I^2$ for a green channel and $I^3$ for a blue channel. With the notations defined above, the calibration operation can be readily presented by a function $f(s,u,v,w)$:

$$\tilde{I}_t^i = f(I_t^i, p_r^i, p_t^i, c^i), \forall t \neq r; t \in [1,2,\ldots T]; r \in [1,2,\ldots T] \quad (1)$$

where $\tilde{I}$ is a color calibrated image. An exemplary function $f(\ )$ could be $$f(s,u,v,w) = s - w \cdot \Phi(u,v) \quad (2)$$

where · is a scalar multiplication operator. Noted that w is a coefficient, $0 \geq w \geq 1$ and it varies for different channels, that is, an adjustable coefficient by the user. Also noted that in Equation (2) s represents an image. The correct interpretation of Equation (2) is that every pixel value in image s will be offset by a quantity of $w \cdot \Phi(u, v)$. It now boils down to determine the function $\Phi(\ )$. As stated previously, the purpose of color calibration is to match the color appearance of one image to that of the other. Therefore, function $\Phi(\ )$ should provide information of the difference between the images to Equation (2). A variety of ways can be used to construct a function $\Phi(\ )$. Below is an exemplary $\Phi(\ )$ function that uses small patches of a common area of the two images:

$$\Phi(u,v) = \zeta(u) - \zeta(v) \quad (3)$$

where $\zeta(\ )$ is a nonlinear function in this exemplary algorithm. A common area such as a portion (507 or 509) of the cheek is a good candidate to extract color difference features between two images. Noted that in practice, it is not necessary for patches 507 and 509 to have the same size or shape. The use of these patches is to provide the algorithm with color (red, green and blue) statistics for the images under processing. There are shown two graphs in FIGS. 6A and 6B. Graph 601 displays three intensity distributions, for red, green and blue respectively, for all the pixels within patch 507 of image 501. Graph 603 displays three intensity distributions, for red, green and blue respectively, for all the pixels within patch 509 of image 503. The color intensity distributions of patch 507 are different from that of patch 509 due to the different lighting conditions for the two images. These color intensity distributions can be used in computing function $\zeta(\ )$. For example, $\zeta(\ )$ could be a function that finds the value that divides the area under the intensity distribution curve into two equal parts. $\zeta(\ )$ also could be a function that finds a trimmed median value of a distribution. The reference patch u could be from any one of the images that acquired in mode 3, or from the first image in mode 2. The color calibration process may also be applied to images acquired in mode 1. Using the algorithm described by Equation (3), the calibrated image of image 503 is obtained and shown in FIG. 5 as image 505 that has a color appearance closer to that of image 501. The skilled in the art should be able to use other previously published color calibration functions than Equation (2) for $f(\ )$.

Figure 4:
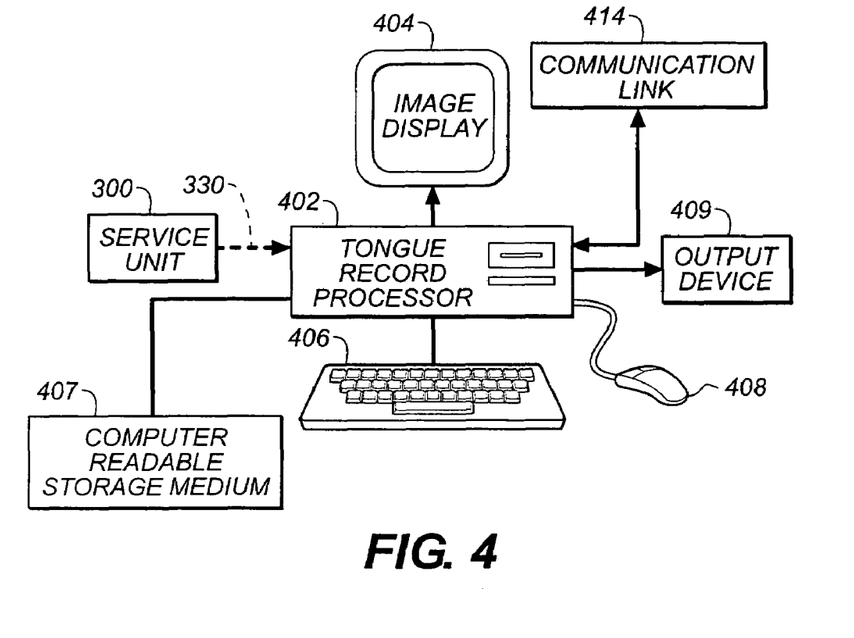
FIG. 4 is a schematic diagram of a tongue record processing hardware system useful in practicing the present invention.

Returning back to FIG. 3A, steps related to data formation and communication will be explained. In the record formation step 304, the acquisition mode is included in the image specific collection data 212. The tongue record is uploaded from the image and data formation unit 300 through the communication step 306 to a processing unit 320 through a link 330. The link 330 could be a wired link or a wireless link. The processing unit 320 could be part of a tongue record processor 402 as shown in FIG. 4. The image and data formation unit 300 also could be part of the tongue record processor 402, in which case, the link 330 is virtually eliminated. In other cases, the tongue record processor 420 can be physically residing in a place proximity to the service unit 300, or in a remote place separated from the unit 300. In either situation, using a wired link is to connect service unit 300 through networks (LANs and/or WANs).

For a wireless link, the wireless communication protocol IEEE-802.11, or one of its successors, is implemented as a choice for this application. This is the standard wireless communications protocol and is the preferred one here. However, while this is preferred, it will be appreciated that this is not a requirement for the present invention, only a preferred operating situation. In wireless connection, service unit 300 may serve as nodes of a LAN or a WAN.

One embodiment of the tongue image inspection system structure of the present invention is a centralized inspection system and illustrated in FIG. 3A in which there are shown four exemplary tongue image and data formation units 300 and one processing unit 320. These tongue image and data formation units 300 could be in places with minimum medical staffing and scattering over a large geographical area. This exemplary structure provides two-way remote messaging and networked communication channels 330. In two-way communications, unit 300 sends tongue records 220 to unit 320 and receives diagnostic information and instructions from unit 320.

Figure 7:
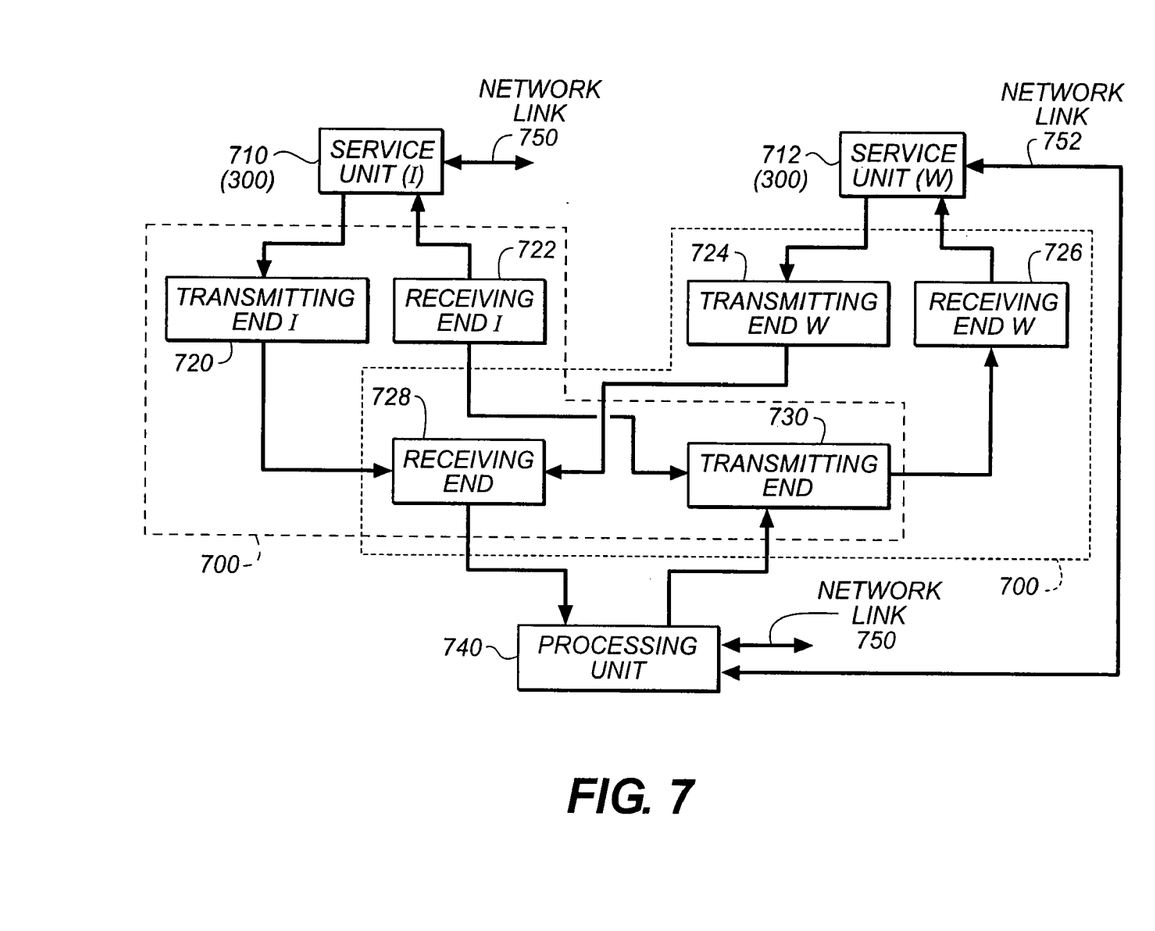
FIG. 7 is a flowchart illustrating a two-way communication system.

An exemplary two-way communication system is shown in FIG. 7. In FIG. 7, service units I (710), through service unit W (712) concurrently capturing and transmitting images. These service units are represented by service unit 300. There are two types of communication links in this exemplary two-way communication system. One of the types is a wireless communication link 700 that has a receiving end and a transmitting end. The other type is a network link 750 through which messages (tongue record, notification message, acknowledgement, or diagnostic message) can be exchanged. Noted that in FIG. 3A, the data communication step 305 performs both receiving and transmitting data tasks, the data input step 306 performs receiving data task, and the data output step 309 performs transmitting data task.

Figure 8:
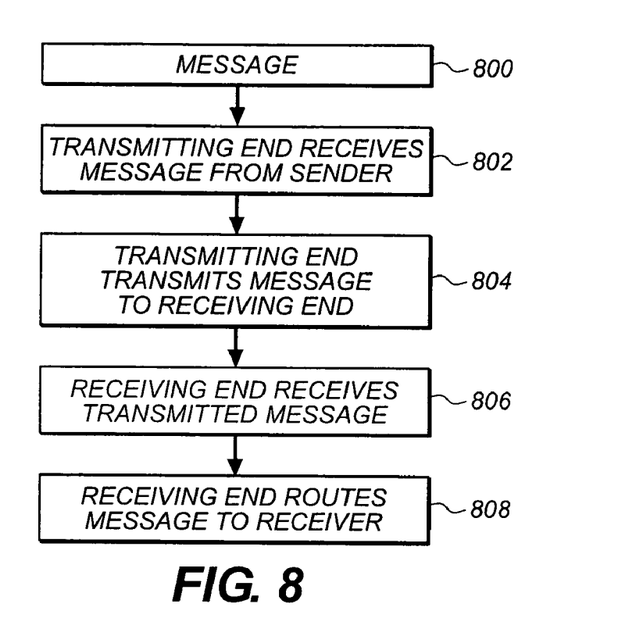
FIG. 8 is a flowchart illustrating two-way communication steps.

For a wireless communication link, FIG. 8 shows a communication path from the transmitting end to the receiving end (such as 720-728, 730-722, 724-728, and 730-726). FIG. 8 represents the steps that take place when a message 800 is transmitted. The message 800 could be the tongue record 220, a notification message from medical staff members at the sites of unit 300, a diagnostic message or an acknowledgment from process unit 320. The communication path receives a message 800 in a step 802 of receiving end receives message from a sender. The message 800 is transmitted in a step 804 of transmitting end transmits message to receiving end. The receiving end receives the transmitted message in step 806 and routes the message to a user (service unit 300) in step 808.

The transmitting and receiving message from the transmitting network (including 802 and 804) to the receiving network (including 806 and 808) is governed by a software platform, which runs on processing unit 740 shown in FIG. 7, to simplify the process of delivering messages to a variety of devices including any mobile computing devices. The software platform service can route and escalate notifications intelligently based on rules set up by the user to ensure "closed loop" communication. Routing rules determine who needs access to information, escalation rules set where the message needs to be directed if the initial contact does not respond, and device priority rules let users prioritize their preferred communication devices. The platform could be designed to use a web-based interface to make using the two-way communication easy. The hosted service uses secure socket layer (SSQ) technology for logins. The software could be designed to run on any operating system and is based on XML (markup language), Voice XML and J2EE (Java 2 Platform, Enterprise Edition). For voice-only device, the software platform can use text-to-voice conversion technology. The message can be received and responded to on any mobile or wireline phone using any carrier or multiple carriers. An exemplary software platform is a commercially available service INlogicNOW developed by MIR3, Inc.

In an exemplary scenario, the remote site receives a notification from the patient site for diagnostic support. The remote site staff launches a software with the patient communication identities such as the IP address. The software then, in tern, launches remote access application using the corresponding IP address through a network link 750 (also 330). After launching the application, a window appears showing exactly what's on the screen of the computer system at the patient side. The health care staff at the remote site can access the patient's computer to open folders and documents residing on the computer, edit them, print them, install or run inspection programs for diagnosis, view images, copy files between the remote site computer and the patient's computer, restart the patient's computer, and so on, exactly as though the health care staff seated in front of patient's computer. The connection is encrypted. With that, the remote site health care staff can perform relevant tasks remotely on service unit 300.

An exemplary realization of direct access network link is by using a commercially available service GoToMyPc from www.gotomypc.com. There is no dedicated compute hardware system needed. Any computer capable of performing image/message processing and accessing the network could be used. That means that the remote site is itself location unconstrained.

Referring to FIG. 3A, the remaining steps of the operation of the tongue inspection system of the present invention are to be further discussed. The step of case retrieval 307, by parsing the tongue record 220 to find the patient's ID, retrieves the patient's previously saved tongue history records, if any, from a data storage server. The retrieved image data is used for the TCM doctor to perform a variety of tasks in the inspect step 308. The data storage server could be a readable storage medium 407 shown in FIG. 4. One of the tasks that the step of inspection 308 performs is the color calibration that is discussed previously.

In step 308, visualization tools are employed for TCM medical professional to examine concerned regions of the object (regions of interest in the images) for better diagnosis. One embodiment of such visualization facility and user interface is illustrated in FIG. 9.

Figure 9:
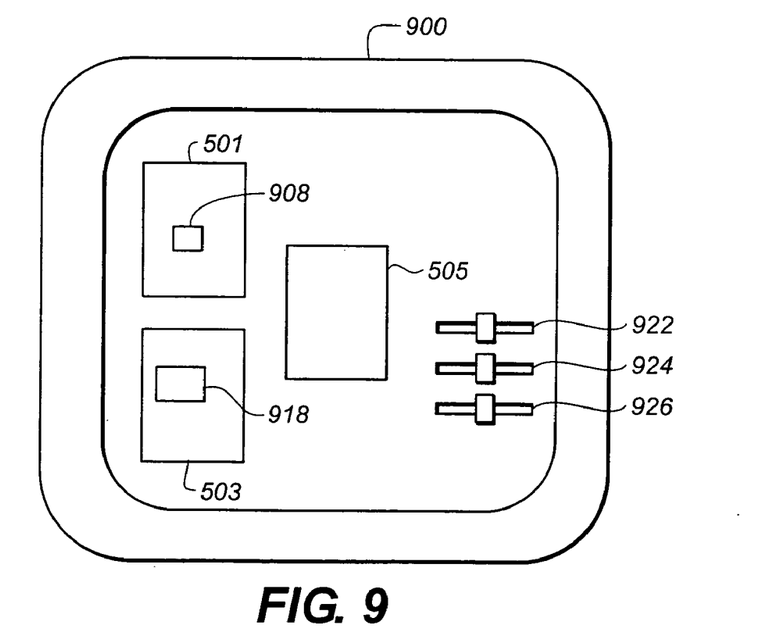
FIG. 9 is a graph illustrating tongue image inspection user interface of the present invention.
Figure 10:
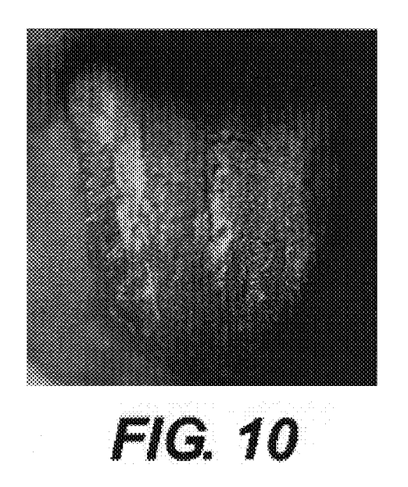
FIG. 10 is an illustration showing a tongue.

There is shown in FIG. 9 a computer monitor screen 900 (also 404 in FIG. 4) hooked up to an image processor (402) that executes previously described steps. On screen 900, two representative image 501 and 503 are shown on the left. Two patches 908 and 918 are selected by the user in order to perform the color appearance calibration. The user is also provided with three bars 922, 924 and 926 to choose coefficient values of w for red, green and blue channels as shown in Equation (2). The calibrated image 505 is shown in the middle of screen 900. It should be pointed out that the color calibration process can run automatically without the user interference. Note that FIG. 9 only illustrates an exemplary usage of the current design. One mode of inspection that step 308 performs is manual diagnosis by a TCM professional. In practice, the TCM professionals are able to retrieve other reference tongue images from the data storage server 407 and display them on the screen as diagnostic guide. An exemplary case discussed in Giovanni Maciocia's book is shown in FIG. 10. The deep red color shows that there is severe heat. The sides are redder and slightly swollen, it is clear that the heat is in the liver. This patient suffered from chronic asthma.

Another mode of inspection that step 308 performs is automatic disease diagnosis by using a classification algorithm that classifies tongue images to normal and abnormal groups. Tongue image features such as color, texture, shape and coating can be used to train a classifier and differentiate normal tongue images from abnormal ones. An exemplary color feature based classification algorithm is described below.

It is known to people skilled in the art that to reduce the brightness influence of brightness component of an image on classification tasks, a color transformation operation is usually applied to a color image before extracting color features. Similar to the color transformation performed in Cai's paper, the current method utilizes a color transformation that converts a color image from the regular RGB space to a generalized RGB space using the formula for every pixel of an image I:

$$\bar{I}^j = \frac{I^j}{\sum_i I^i}; i \in [1, 2, 3]; j \in [1, 2, 3] \tag{4}$$

where $\bar{I}^x$ is a color plane (channel) of the resultant generalized RGB image and $I^x$ is a color plane (channel) of an RGB color image as previously defined. For every pixel of $\bar{I}$, the resultant three new elements are linearly dependent, that is, $$\sum_j \bar{I}^j = 1,$$

so that only two elements are needed to effectively form a new space that is collapsed from three dimensions to two dimensions. In most cases, $\bar{I}^1$ and $\bar{I}^2$, that is, generalized R and G, are used. Noted that for simplicity, in the above discussion, an image and a pixel of that image share a single notation.

In order to train a classifier, a plurality of tongue images (from both healthy and unhealthy people) must be collected and the tongue regions (see example of tongue region 502 in FIG. 5) are segmented from all the collected tongue images. Methods such as reported by Bo Pang (see "On Automated Tongue Image Segmentation in Chinese Medicine," Bo Pang, et al., Proc. ICPR, 2002) can be used to effectively extract tongue regions from the tongue images. Pixels of the extracted tongue regions are then converted from the RGB space to the generalized RGB space as described above. Denote the components of the converted color pixel by if; $\bar{q}^i$:j=[1,2,3]. Denote $\hat{\theta}_n=[\bar{q}_n{}^1,\bar{q}_n{}^2]$ as the color feature vector for a pixel from the tongue region of a healthy people. Denote $\bar{\theta}_a=[\bar{q}_a{}^1,\bar{q}_a{}^2]$ as the color feature vector for a pixel from the tongue region of an unhealthy people. Color feature vectors $\hat{\theta}_n$ and $\hat{\theta}_a$ will be used in a supervised learning process to train a classifier.

A supervised learning is defined as a learning process in which the exemplar set consists of pairs of inputs and desired outputs. In this tongue image classification case, the exemplar inputs are $\hat{\theta}_n$ and $\hat{\theta}_a$, the exemplar desired outputs are indicators $O_n$ and $O_a$ for normal and abnormal respectively. Suppose that there are M color feature vectors $\hat{\theta}$ among which, $M_n$ vectors (denoted by $\hat{\theta}_n{}^i$, i=1 . . . $M_n$) represent normal condition with indicator $O_n$, and $M_a$ vectors (denoted by $\hat{\theta}_n{}^i$, i=1 . . . $M_a$) represent abnormal condition with indicator $O_a$. These learned vectors $\hat{\theta}_n{}^i$ and $\hat{\theta}hd a^i$ are used to train a classifier that in turn is used to classify a tongue image in a detection or diagnosis process.

For the learning and training purpose, construct the training data set $$\{p_j\tau_j\}, j=1\ldots l, \tau_j=\{-1,1\}, p_j \in \Re^d \quad (5)$$

wherein $\tau_j$ are the class labels.

For example, if the condition is normal, $\tau_j=1$, otherwise, $\tau_j=-1$. The vector $p_j=[\hat{\theta}]$ is traditionally called feature vector in computer vision literature. The notion $\Re^d$ represents a domain, d is the domain dimension. For this exemplary case, d=2. Persons skilled in the art understand that the data vector $p_j$ can be constructed in a different manner and augmented with other physical (texture, coating, etc.) numerical elements.

There are known types of classifiers that can be used to accomplish the task of differentiating normal tongue images from abnormal ones with the use of color feature vectors. An exemplary classifier is an SVM (support vector machine) (refer to "A Tutorial on Support Vector Machines for Pattern Recognition," by C. Burges, *Data Mining and Knowledge Discovery*, 2, 121-167, 1998, Kluwer Academic Publisher, Boston).

An example case of an SVM classifier would be training and classification of data representing two classes that are separable by a hyper-plane. A hyper-plane that separates the data satisfies $$W \cdot p + \sigma = 0$$

where $\cdot$ is a dot product.

The goal of training the SVM is to determine the free parameter W and $\sigma$. A scaling can always be applied to the scale of W and $\sigma$ such that all the data obey the paired inequalities:

$$\tau_j(W \cdot p_j + \sigma) - 1 \leq 0, \forall j \quad (6)$$

Equation (6) can be solved by minimizing a Lagrangian function $$L(W,\xi) = \frac{1}{2}\|W\|^2 - \sum_{j=1}^{l} \xi_j(\tau_j(W \cdot p_j + \sigma)) \quad (7)$$

with respect to the parameter W, and maximize it with respect to the undetermined multipliers $\xi_j \leq 0$.

After the optimization problem has been solved, the expression for W in Equation (6) can be rewritten in terms of the support vectors with non-zero coefficients, and plugged into the equation for the classifying hyper-plane to give the SVM decision function:

$$\Psi(p_{new}) = (W \cdot p_{new} + \sigma) = \sum_{j=1}^{l_s} \tau_j \xi_j p_j \cdot p_{new} + \sigma \quad (8)$$

wherein $l_s$ is the number of support vectors. Classification of a new vector $p_{new}$ into one of the two classes (normal and abnormal) is based on the sign of the decision function. Persons skilled in the art will recognize that in non-separable case, non-linear SVMs can be used.

Also recognized is that other sophisticated tongue image classification methods such as Bayesian Network based algorithms are available in the public domain (see "Computerized Tongue Diagnosis Based on Bayesian Networks," by Bo Pang, David Zhang, Naimin Li, and Kuanquan Wang, *IEEE Transactions on Biomedical Engineering*, No. 10, Vol. 51, October 2004).

Noted that the tongue image classification can be accomplished automatically with no user interference. The classification process can also be accomplished with the help from the user with a user interface such as the one shown in FIG. 9 for image segmentation. In either case, the task can be performed using the tongue record processor 402 in FIG. 4. The classification results will be incorporated into tongue record 220 in a step of tongue record updating 308.

For completeness, FIG. 4 shows an exemplary of a tongue image inspection hardware system useful in practicing the present invention including a service unit 300. The images from the service unit 300 is provided to a tongue record processor 402, such as a personal computer, or work station such as a Sun Sparc workstation. The tongue record processor 402 preferably is connected to a CRT display 404, an operator interface such as a keyboard 406 and a mouse 408. The tongue record processor 402 is also connected to computer readable storage medium 407. The tongue record uploading step 312 shown in FIG. 3A can update 310 the patient history that is stored in medium 407. The tongue record processor 402 transmits processed digital images and metadata to an output device 409. Output device 409 can comprise a hard copy printer, a long-term image storage device, and a connection to another processor. The tongue record processor 402 is also linked to a communication link 414 or a telecommunication device connected, for example, to a broadband network.

The invention has been described in detail with particular reference to certain preferred embodiments thereof, but it will be understood that variations and modifications can be effected within the spirit and scope of the invention.

PARTS LIST 101 image
102 ColorChecker plate
104 tongue
204 general metadata
206 image packet
208 pixel data
210 image specific metadata
212 image specific collection data
216 inferred image specific data
220 tongue record
300 service unit
302 tongue image acquisition
304 tongue record formation
305 data communication
306 data input
307 case retrieval
308 inspection
309 data output
310 tongue recorder updating
312 tongue record uploading
320 process unit
330 communication link
402 tongue record processor
404 image display
406 data and command entry device
407 computer readable storage medium
408 data and command control device
409 output device
414 communication link
501 image
502 tongue
503 image
505 image
507 patch
509 patch
601 graph
603 graph
700 two way notification system
710 service unit I
712 service unit W
720 transmitting end I
722 receiving end I
724 transmitting end W
726 receiving end W
728 receiving end
730 transmitting end
740 processing unit
750 network link
752 network link
800 message
802 step
804 step
806 step
808 step
900 screen
908 patch
918 patch
922 bar
924 bar
926 bar

The invention claimed is:

1. A method for diagnosing diseases by inspecting images of an individual's tongue comprising:

forming a first image of said tongue, a color checker, and a portion of said individual's face;

forming a second image of said tongue and said portion of said individual's face;

performing a color comparison of said portion of said individual's face in said second image to said portion of said individual's face in said first image;

matching the colors in said second image to the colors in said first image based on said color comparison; and diagnosing at least one disease based on changes in said first tongue image and said second tongue image.

2. The method as in claim 1 wherein a color calibration is performed on said first image prior to said color comparison step.

3. The method of claim 1 wherein said diagnosis is aided by comparison to reference images of other individuals tongues.

4. A method for diagnosing diseases by inspecting images of an individual's tongue comprising:

forming a first image of said tongue and a portion of said individual's face;

forming a second image of said tongue and said portion of said individual's face;

performing a color comparison of said portion of said individual's face in said second image to said portion of said individual's face in said first image;

matching the colors in said second image to the colors in said first image based on said color comparison; and diagnosing at least one disease based on changes in said first tongue image and said second tongue image.

5. The method of claim 4 comprising the additional steps of:

forming a third image of said tongue, said portion of said individual's face, and a color checker;

performing a color calibration on said third image;

performing a color comparison of said portion of said individual's face in said third image to said portion of said individual's face in said first and second image; and matching the colors in said first and second image to the colors in said third image based on said color comparison.

6. The method of claim 4 comprising the additional steps of:

transmitting said first image and said second image to a process unit; and performing said diagnosis step at said process unit.

7. The method of claim 1 further comprising the steps of:

retrieving the patient's tongue history records from an image storage facility;

reviewing and classifying the first or second image of said tongue and the retrieved history records;

transmitting, displaying, or storing the classification, or tongue records.

8. The method of claim 7 wherein the step of classifying the acquired and retrieved tongue images using an inspection mode further comprises the steps of:

collecting a plurality of sample tongue images from healthy and unhealthy individuals;

extracting relevant color information from said plurality of sample tongue images in a transformed color space;

extracting relevant non-color information from said plurality of sample tongue images;

training classifiers with the extracted color and non-color information; and applying the trained classifiers to the acquired at least one image of a patient tongue.

* * * * *